(12) United States Patent
Merz et al.

(10) Patent No.: US 8,847,339 B2
(45) Date of Patent: Sep. 30, 2014

(54) INTEGRATED CIRCUIT

(71) Applicant: NXP B. V., Eindhoven (NL)

(72) Inventors: Matthias Merz, Leuven (BE); Aurelie Humbert, Brussels (BE); David Tio Castro, Oud Heverlee (BE)

(73) Assignee: NXP B.V., Eindhoven (NL)

( * ) Notice: Subject to any disclaimer, the term of this patent is extended or adjusted under 35 U.S.C. 154(b) by 0 days.

(21) Appl. No.: 13/751,365

(22) Filed: Jan. 28, 2013

(65) Prior Publication Data

US 2013/0214274 A1 Aug. 22, 2013

(30) Foreign Application Priority Data

Feb. 17, 2012 (EP) ..................................... 12156028

(51) Int. Cl.
*H01L 29/82* (2006.01)
(52) U.S. Cl.
USPC ............ 257/415; 257/48; 257/414; 257/417; 257/419; 438/52; 438/53
(58) Field of Classification Search
USPC .................. 257/48, 414–415; 438/22, 48–52, 438/E21.002, E29.166; 73/31.05–31.06
See application file for complete search history.

(56) References Cited

U.S. PATENT DOCUMENTS

| | | | |
|---|---|---|---|
| 4,257,061 A | 3/1981 | Chapel, Jr. et al. | |
| 5,596,219 A | 1/1997 | Hierold | |
| 8,109,130 B2 * | 2/2012 | Dimeo et al. | ............... 73/31.05 |
| 8,354,729 B2 * | 1/2013 | Hsieh et al. | .................. 257/414 |
| 2006/0205106 A1 | 9/2006 | Fukuda et al. | |
| 2009/0151429 A1 * | 6/2009 | Jun et al. | ...................... 73/31.06 |
| 2010/0075481 A1 | 3/2010 | Yang | |
| 2011/0012211 A1 * | 1/2011 | Merz et al. | ..................... 257/415 |

OTHER PUBLICATIONS

Baltes, Henry et al., "CMOS as Sensor Technology"; Sensors and Actuators A, vol. 37-38, Elsevier, Lusance, CH; pp. 51-56; (Jun. 1, 1993).
Swart, Nicholas R., et al.; "An Integrated CMOS Polysilicon Coil-Based Micro-Pirani Gauge with High Heat Transfer Efficiency"; Int'l Electron Devices Meeting, 1994, Technical Digest , San Francisco, CA, US; IEEE, New York, NY, US; pp. 135-138 (Dec. 11, 1994).
Kuntner, J, et al.; "Simultaneous Thermal Conductivity and Diffusivity Sensing in Liquids Using a Micromachined Device"; Sensors and Actuators, vol. 130-131, Elsevier, Lausanne, CH; pp. 62-67 (Aug. 14, 2006).
Kaltsas, Grigoris, et al.; Study and Evaluation of a PCB-MEMS Liquid Microflow Sensor; Sensor 2010, 21 pages; (Oct. 8, 2010).
van Herwaarden, Sander; "Thermal Conductivity Gauge for Gas Type Measurement and Vacuum Measurement"; Xensor Integration; 22 pages (Oct. 12, 2010).
Kliche, K., et al; "Sensor for Gas Analysis Based on Thermal Conductivity, Specific Heat Capacity and Thermal Diffusivity"; MEMS 2011, Cancun, Mexico; IEEE, New York, NY, US; pp. 1189-1192 (Jan. 2011).
Extended European Search Report for Application 12156028.8 (Jul. 26, 2012).

* cited by examiner

*Primary Examiner* — Dung A. Le

(57) ABSTRACT

Disclosed is an integrated circuit comprising a substrate (10) including semiconductor devices and a metallization stack (20) over said substrate for interconnecting said devices, the metallization stack comprising a cavity (36), and a thermal conductivity sensor comprising at least one conductive portion (16, 18) of said metallization stack suspended in said cavity. A method of manufacturing such an IC is also disclosed.

15 Claims, 9 Drawing Sheets

INTEGRATED CIRCUIT

CROSS-REFERENCE TO RELATED APPLICATIONS

Figure 1:
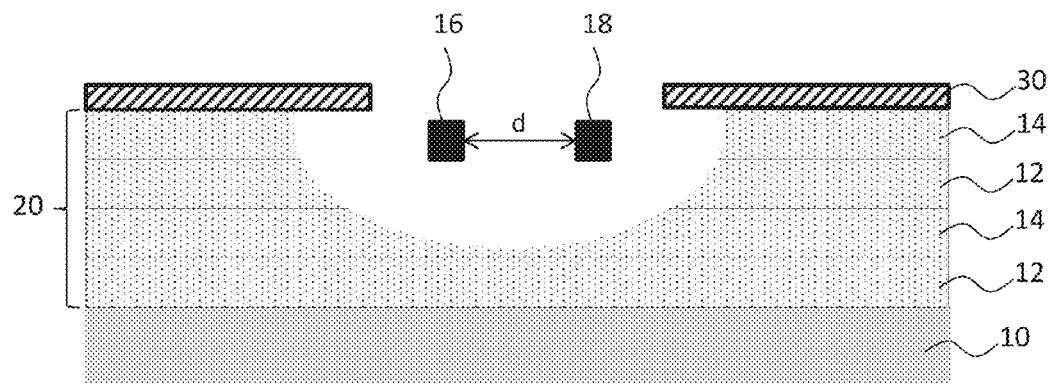

This application claims the priority under 35 U.S.C. §119 of European patent application no. 12156028.8, filed on Feb. 17, 2012, the contents of which are incorporated by reference herein.

FIELD OF THE INVENTION

Embodiments of the present application relate to an integrated circuit (IC) including a sensor.

Embodiments of the present application further relate to a method of manufacturing such an IC.

BACKGROUND OF THE INVENTION

Nowadays, many ICs comprise sensor functionality, as the demand for greater multifunctionality of the IC increases. Parameters to be measured by such sensors may include temperature, relative humidity, moisture, presence and/or concentration of a chemical compound in a sample, and so on. Such sensors find applicability in a wide range of application domains, including medical devices and assays, automotive, smart homes, food packages and more. It is of course commercially interesting to integrate sensor functionality into an IC as it reduces the complexity and foot print of the overall sensing system, and can mean a significant cost saving over discrete components.

To this end, it is desirable that additional sensing functionality can be added to an IC without having to alter the IC manufacturing process. This may often prove practically impossible, in which case this objective translates into adding the smallest number of alterations as possible to the standard process flow to limit the added cost of the required functionality to the IC design.

A particular example of sensing functionality that can be added to an IC design is a thermal conductivity sensor. Such a sensor may be used to determine the composition and/or pressure of a fluid such as a gas or a liquid. The principle of such a sensor is for instance explained in a paper by Nicholas R. Swart et al. in Electron Devices Meeting, 1994, IEDM '94, Technical Digest, International on pages 135-138. In this paper, a polysilicon coil-based micro-Pirani gauge is disclosed in which a pair of meandering polysilicon coils is formed in a silicon substrate of a CMOS IC. The heat transfer from the active to the passive coil is measured, with the amount of heat transfer being governed by the thermal conductivity of the gas in between the two coils.

The sensing coil essentially is operated by the determination of the resistance of the coil at a given current through the coil, which is temperature-dependent. The determination of the resistance and hence the temperature of the coil can be used to determine the heat transfer from the active coil to the passive coil, as $R=R_0(1+a(T+T_0))$, in which $R_0$ is the absolute resistance of the coil at temperature $T_0$, R is the measured resistance, a is the temperature coefficient of the resistance and T is the actual temperature at which R has been determined.

The micro-Pirani gauge disclosed by Swart et al. suffers from a number of drawbacks. Most notably, the formation of the coils in the substrate compromises the integrated density of semiconductor devices of the IC, which is not ideal when silicon real estate comes at a premium. Moreover, the fact that both coils are formed of polysilicon, i.e. have the same temperature coefficient of resistance, limits the sensitivity of the thermal conductivity sensor.

SUMMARY OF THE INVENTION

U.S. Pat. No. 5,596,219 describes a semiconductor component with monolithically integrated electronic circuits and monolithically integrated sensor/actuator, whereby the sensor/actuator is manufactured with methods of surface micromachining in a sensor layer of polysilicon that is structured, for example, with sensor webs, and these sensor webs are thermally insulated from a silicon substrated by a cavity that is produced in a sacrificial layer and is closed gas-tight toward the outside with a closure layer.

US 2006/0205106 A1 describes an integrated MEMs and a method of manufacture thereof.

US2011/0012211 A1 describes a semiconductor device comprising a stack of patterned metal layers separated by dielectric layers, said stack comprising a first conductive support structure and a second conductive support structure and a cavity in which an inertial mass element comprising at least one metal portion is conductively coupled.

U.S. Pat. No. 4,257,061 describes a thermally isolated monolithic semiconductor die.

Embodiments of the present application seek to overcome at least some of the aforementioned problems.

According to an aspect, there is provided an integrated circuit comprising a substrate including semiconductor devices and a metallization stack over said substrate for interconnecting said devices, the metallization stack comprising a cavity, and a thermal conductivity sensor comprising at least one conductive portion of said metallization stack suspended in said cavity.

This allows for the inclusion of a thermal conductivity sensor in the design of an IC without the need to sacrifice substrate area, whilst at the same providing the ability to form the conductive portion in suitable conductive materials, e.g. one or more metals.

In an embodiment, at least some of the semiconducting devices define a control circuit for determining the resistance of the conductive portion at a predefined voltage or current across the conductive portion such that the thermal conductivity sensor may be controlled by integrated circuits.

The at least one conductive portion may be formed in a metal layer or a via layer of the metallization stack, such that different materials may be exploited.

The metallization stack may comprise a metal plate located in between the at least one conductive portion and the substrate to protect the substrate from damage during the formation of the cavity in the metallization stack.

In an embodiment, the thermal conductivity sensor comprises at least a pair of conductive portions including a sensing element and a separate heating element suspended in said cavity, said sensing element being thermally coupled to the heating element. This improves the accuracy of the heat conductivity measurement performed with the thermal conductivity sensor.

The heating element and the sensing element may be formed in the same layer of the metallization stack. This gives good flexibility in the design of the thermal conductivity sensor, as the distance between the heating element and the sensing element can be tuned independent of the spacing rules (i.e. required thicknesses) of the various layers in the metallization stack.

In an embodiment, the heating element and sensing element are interdigitated to provide an effective thermal coupling between the heating element and the sensing element.

Alternatively, the heating element and the sensing element may be formed in different layers of the metallization stack. For instance, one of the heating element and the sensing element may be formed in a via layer. This may be advantageous when the via layer comprises tungsten, as tungsten has a higher specific resistance then most metals used in the metal layers of the metallization stack, such that a larger response signal is obtained upon a change in temperature or fluid composition to which the thermal conductivity sensor is exposed.

In another embodiment, the thermal conductivity sensor further comprises a further sensing element suspended in said cavity at a distance to the heating element that is different to the distance between the heating element and the sensing element. Such a configuration is for instance suitable for differentiation measurements and/or dynamic flow measurements.

The heating element and/or the sensing element may have a meandering shape to optimize its area.

In order to improve the stability of the at least one conductive portion, the metallization stack may comprise a multi-layered support structure for supporting the at least one conductive portion.

Embodiments of the IC as described in this application may find their application in a wide variety of application domains, such as smart buildings, home automation, HVAC systems, supply chain monitoring, e.g. perishables in a modified atmosphere, gas monitoring in medical devices such as breathing machines and so on. To this end, embodiments of the IC as described in this application may be comprised in an article such as an electronic device, a vehicle, a food package, a medical apparatus such as a breathing machine and so on.

According to another aspect, an embodiment of a method of manufacturing an integrated circuit comprising a thermal conductivity sensor is provided, in which the method comprises providing a substrate including a plurality of semiconductor elements; forming a metallization stack on said substrate for interconnecting said semiconductor elements, said metallization stack comprising at least one conductive portion of said sensor; forming a passivation layer over the metallization stack; opening the passivation layer to expose selected portions of the metallization stack; and exposing the selected portions to at least one etch recipe to form a cavity such that the at least one conductive portion is suspended in said cavity.

Such an IC may be formed in many existing semiconductor device manufacturing processes using available processing steps such that the thermal conductivity sensor can be integrated without significantly adding to the cost of the IC.

BRIEF DESCRIPTION OF THE EMBODIMENTS

Figure 2:
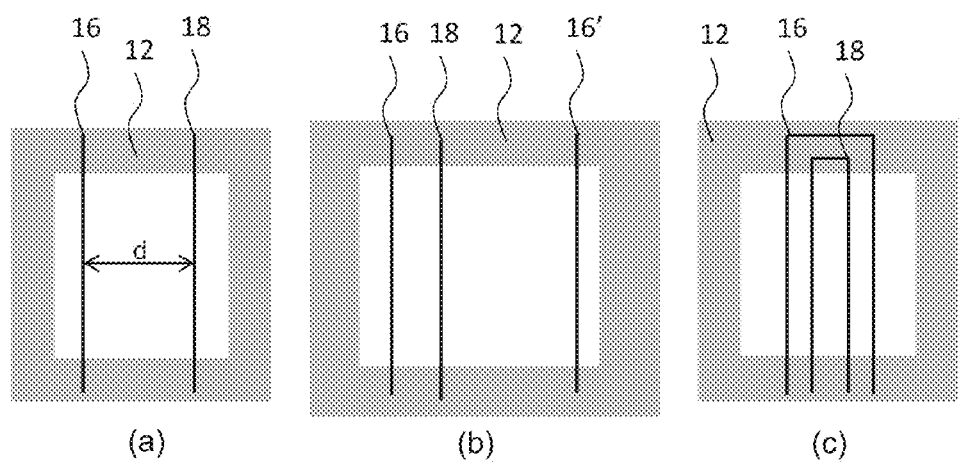
Figure 3:
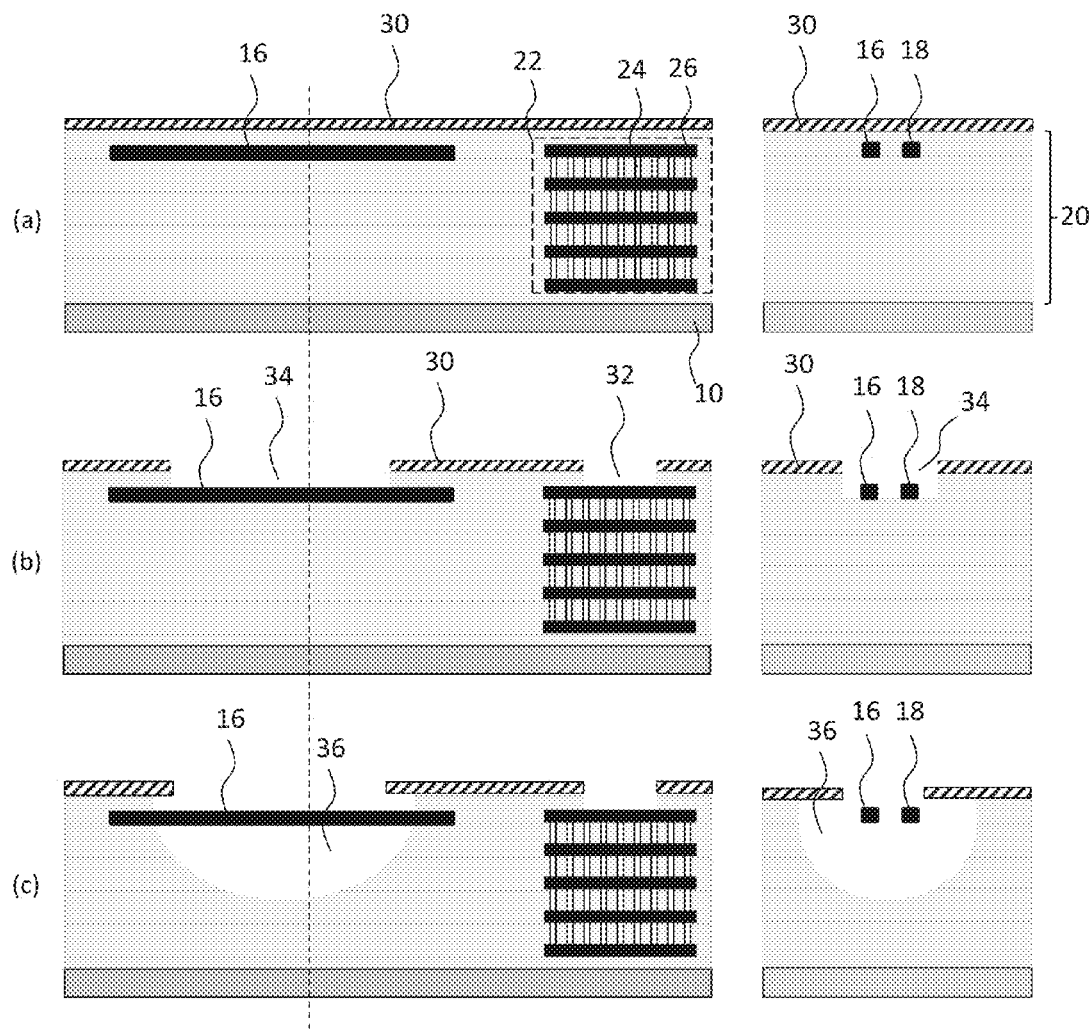
Figure 4:
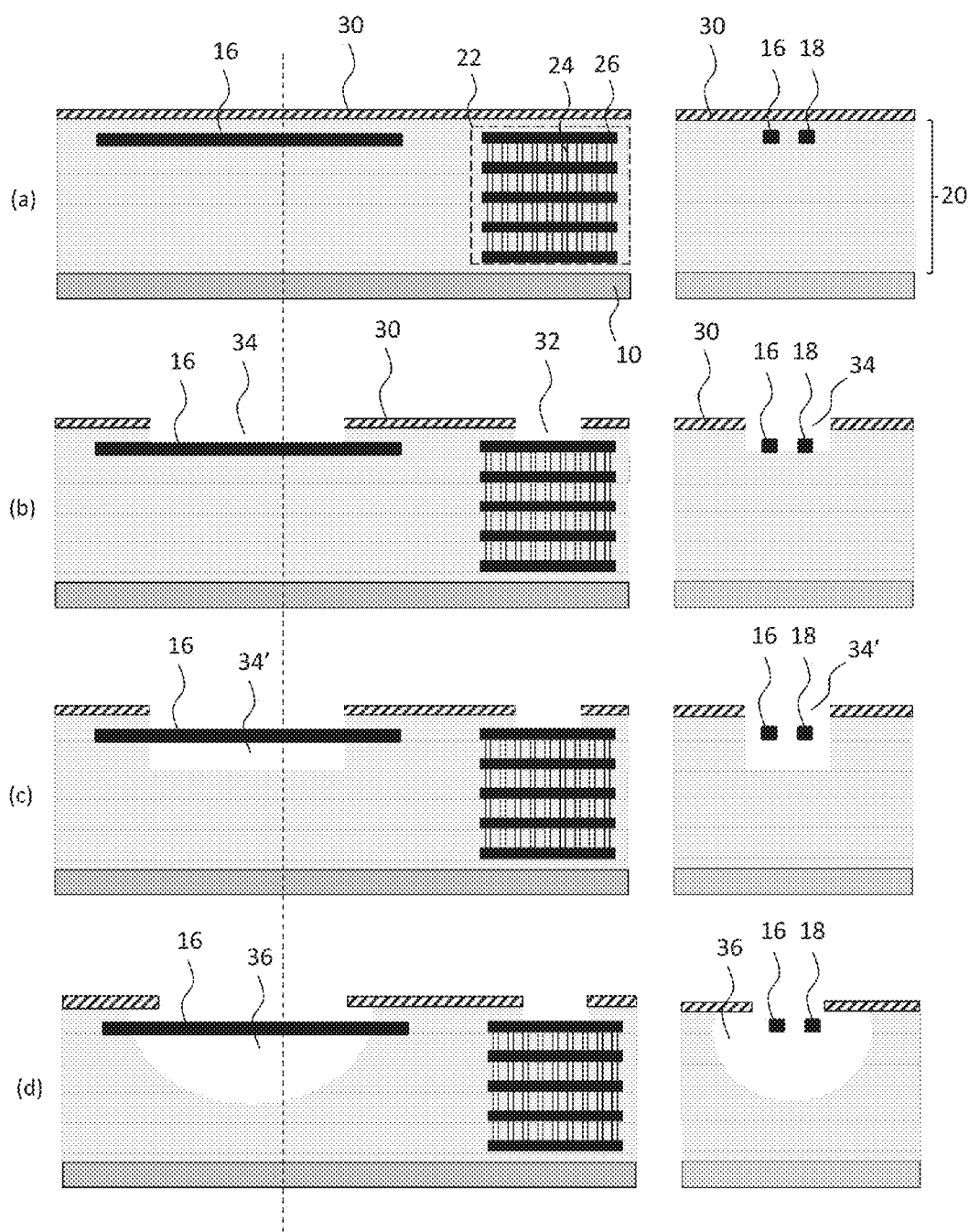
Figure 5:
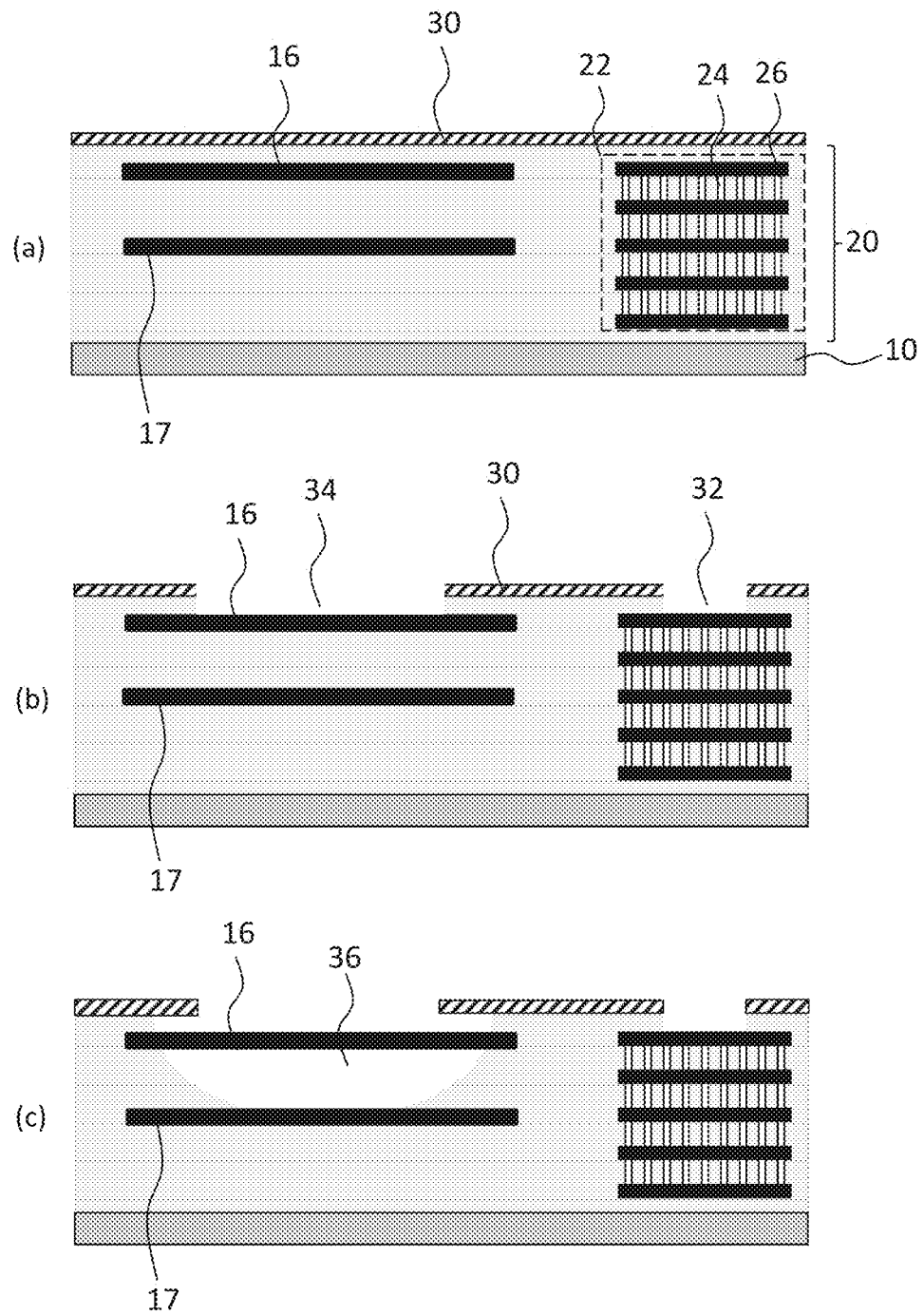
Figure 6:
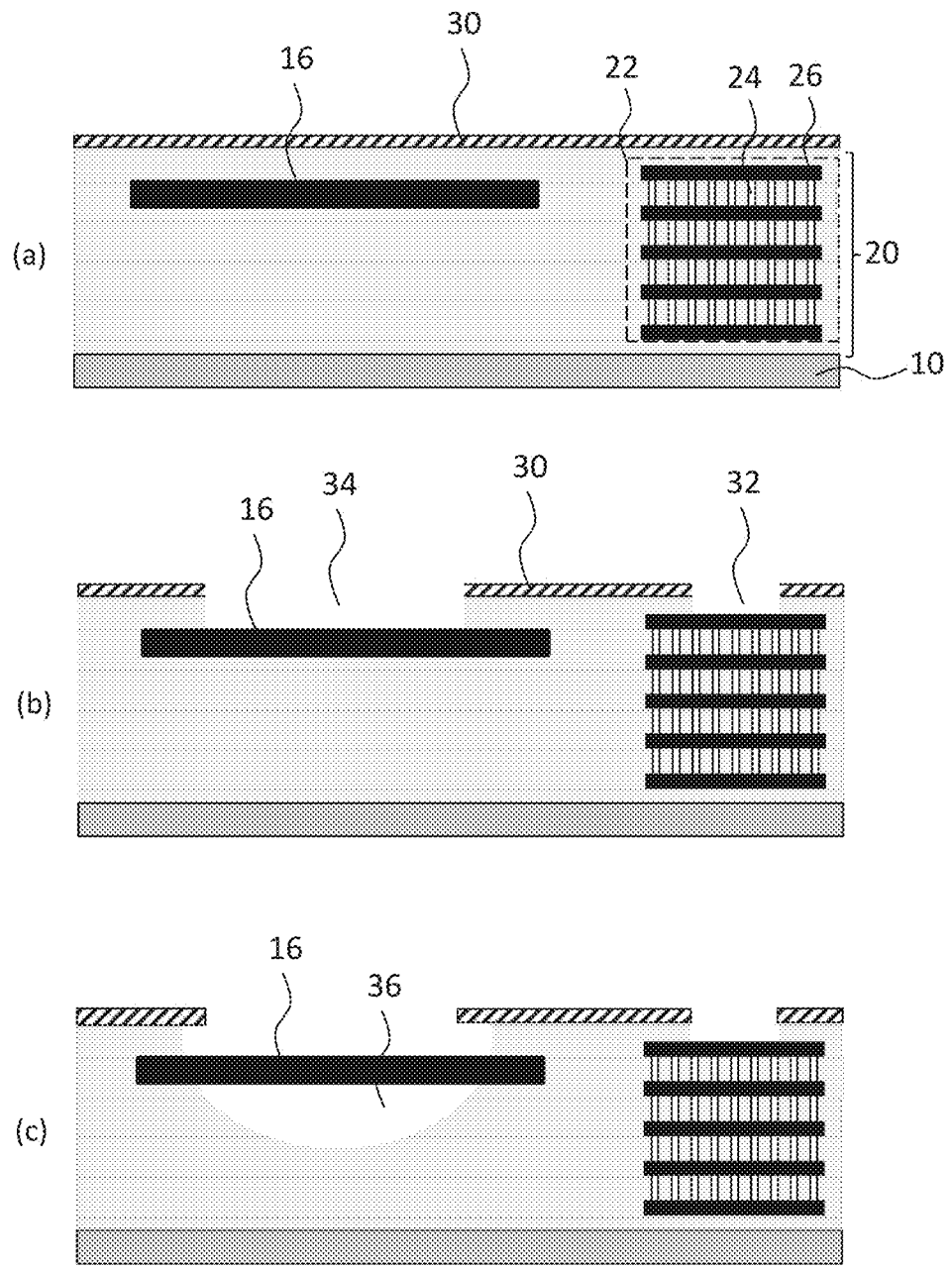
Figure 7:
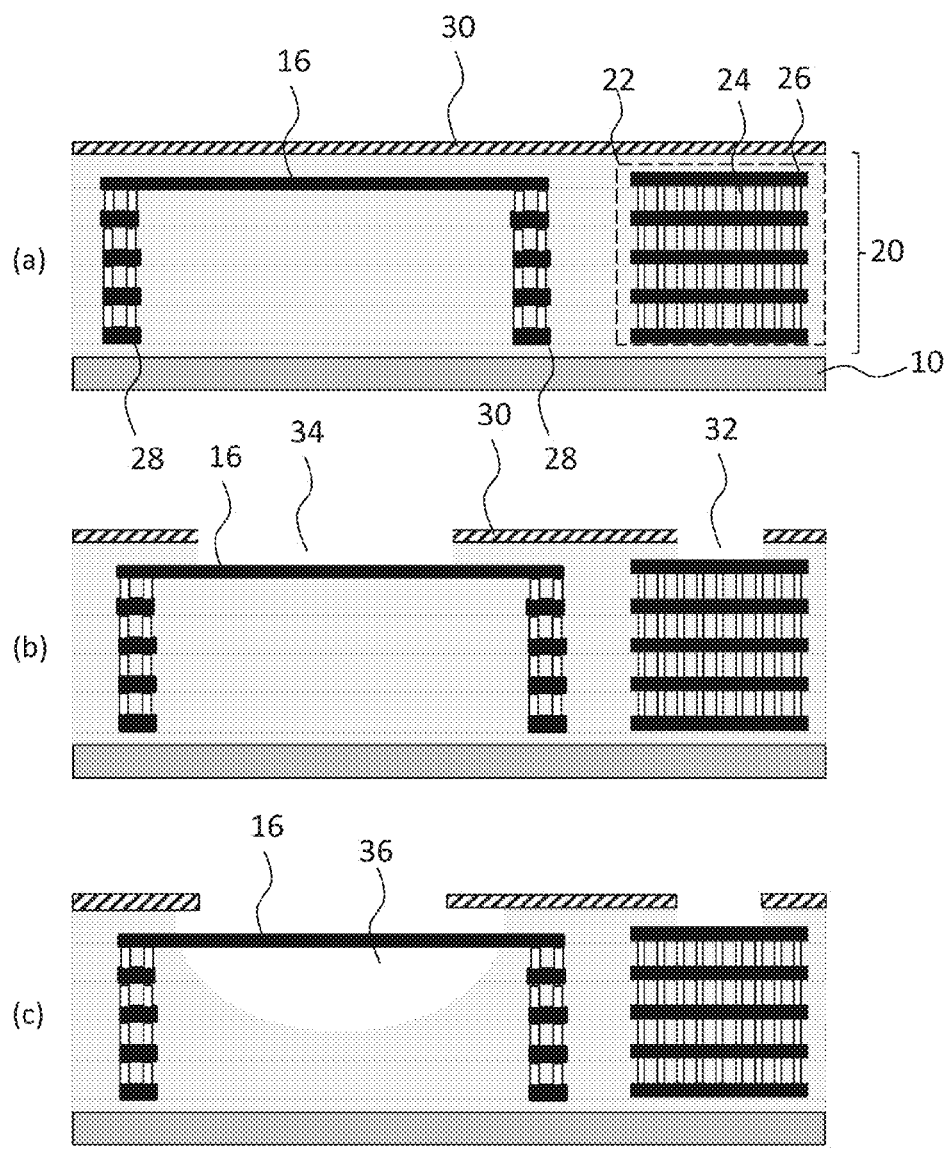
Figure 8:
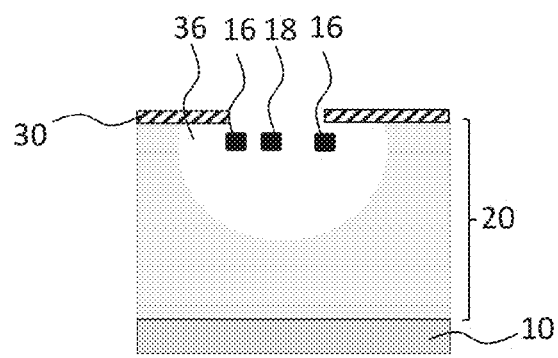
Figure 9:
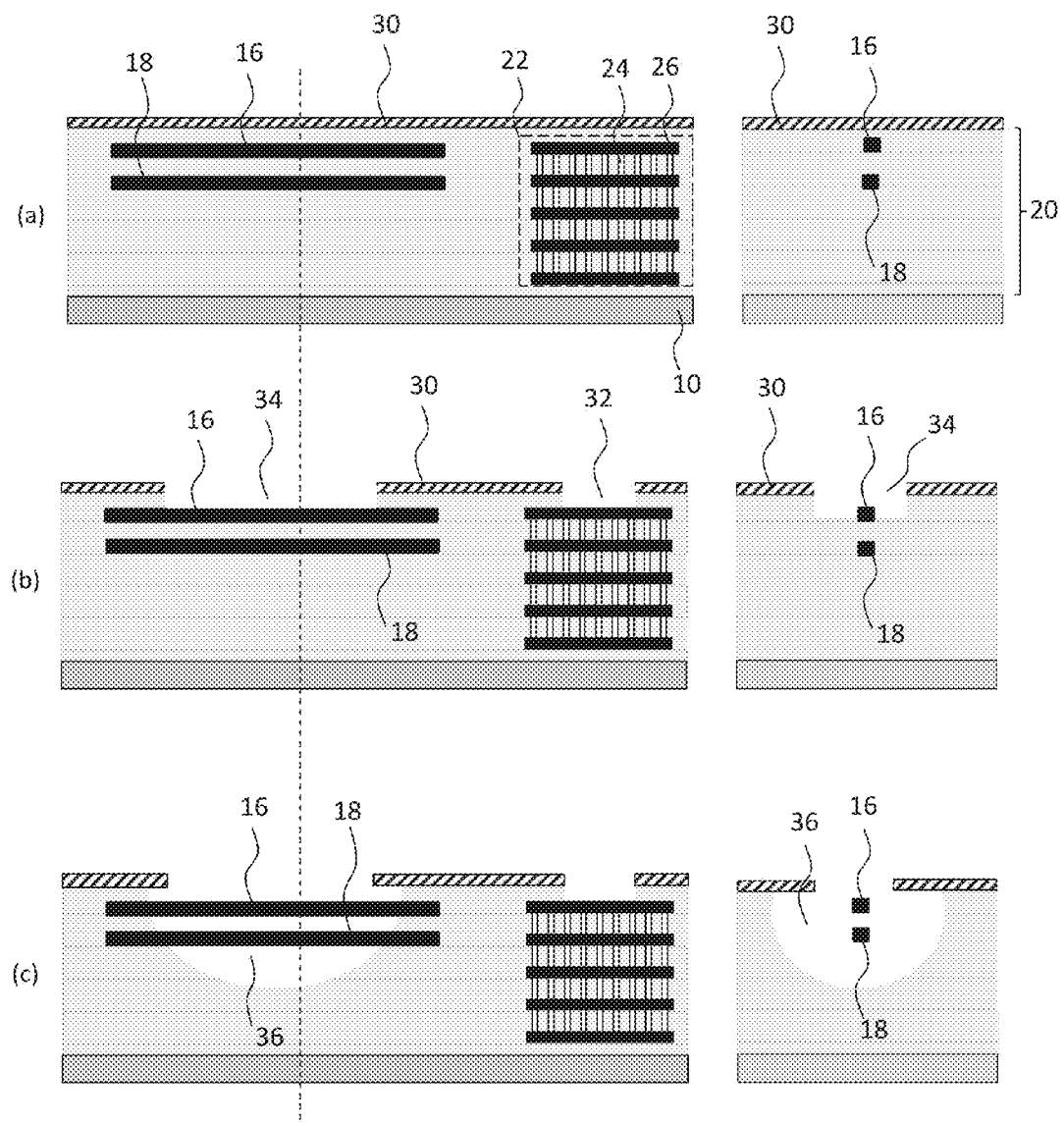
Figure 10:
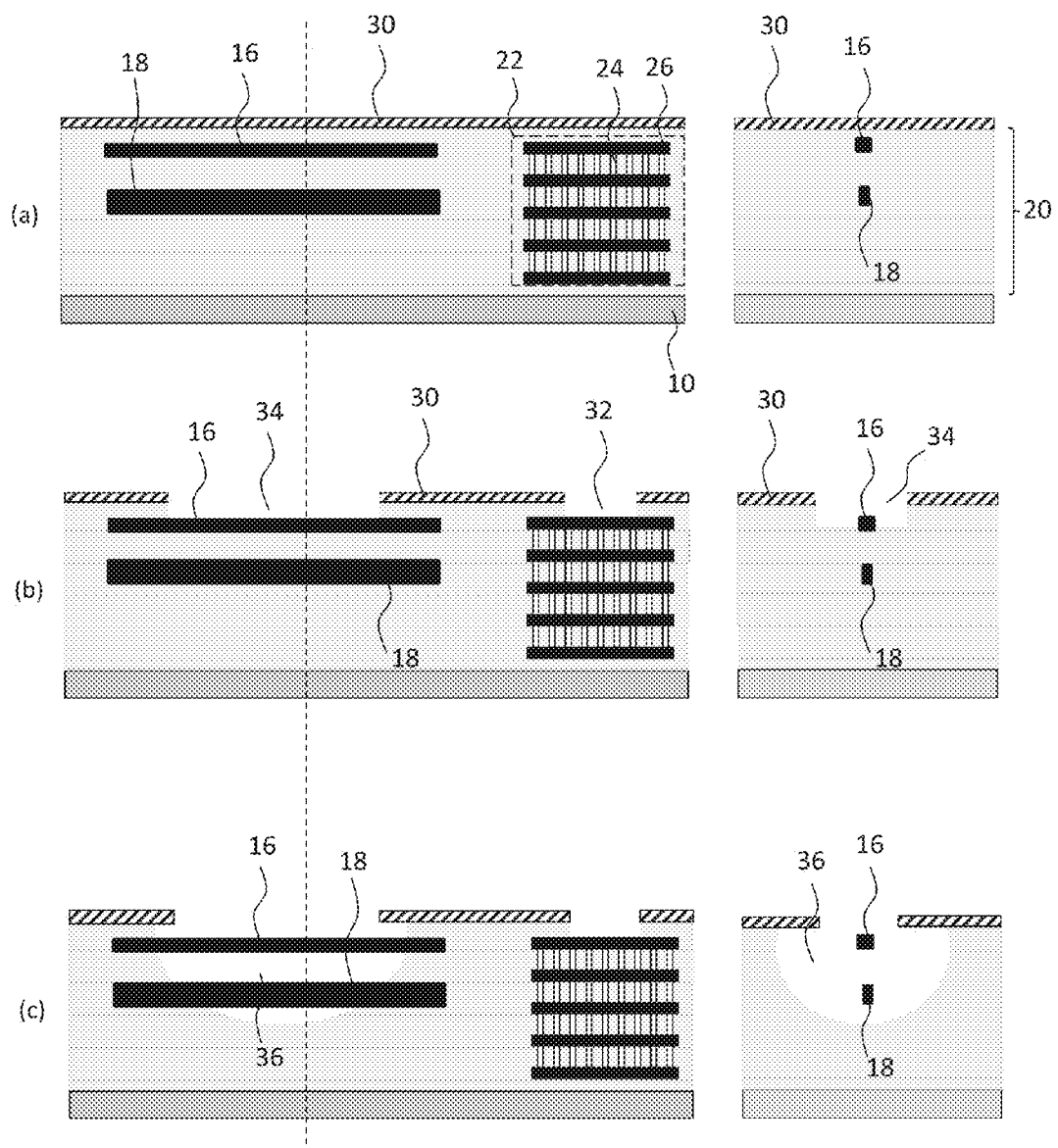
Figure 11:
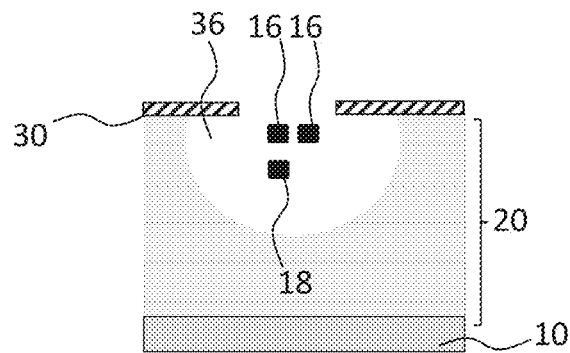
Figure 12:
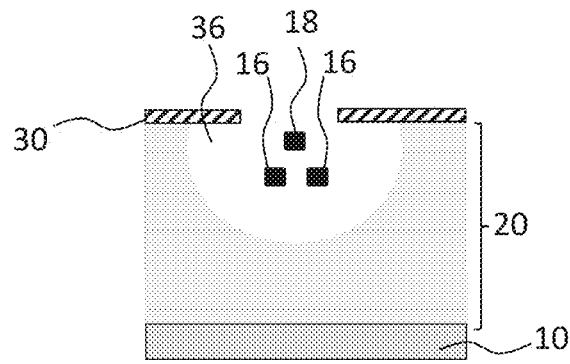
Figure 13:
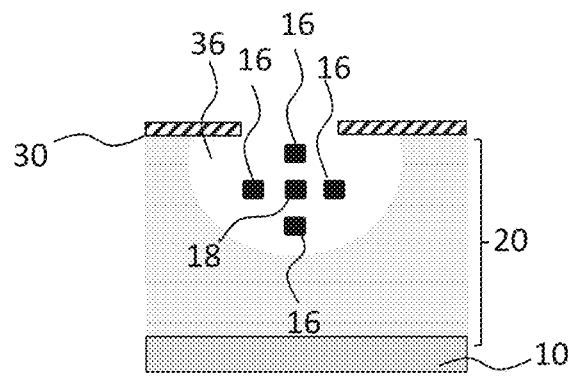

Embodiments of the invention are described in more detail and by way of non-limiting examples with reference to the accompanying drawings, wherein:

FIG. 1 schematically depicts an embodiment of an IC with a thermal conductivity sensor;

FIG. 2 schematically depicts a number of non-limiting example layouts of such a thermal conductivity sensor;

FIG. 3 schematically depicts an embodiment of a method of forming an IC with a thermal conductivity sensor;

FIG. 4 schematically depicts an alternative embodiment of a method of forming an IC with a thermal conductivity sensor;

FIG. 5 schematically depicts another embodiment of a method of forming an IC with a thermal conductivity sensor;

FIG. 6 schematically depicts yet another embodiment of a method of forming an IC with a thermal conductivity sensor;

FIG. 7 schematically depicts yet another embodiment of a method of forming an IC with a thermal conductivity sensor;

FIG. 8 schematically depicts another embodiment of an IC with a thermal conductivity sensor;

FIG. 9 schematically depicts a further embodiment of a method of forming an IC with a thermal conductivity sensor;

FIG. 10 schematically depicts a yet further embodiment of a method of forming an IC with a thermal conductivity sensor; and FIG. 11-13 depict various non-limiting example embodiments of an IC with a thermal conductivity sensor.

DETAILED DESCRIPTION OF THE DRAWINGS

It should be understood that the Figures are merely schematic and are not drawn to scale. It should also be understood that the same reference numerals are used throughout the Figures to indicate the same or similar parts.

In the context of the present application, a metallization stack is a layer structure comprising various patterned metal layers separated from each other by electrically insulating (dielectric) layers through which conductive conduits such as vias may be formed to interconnect metal portions in different layers with each other. A metallization stack may be used to provide the electrical interconnections between semiconductor devices in or on a substrate and/or between a semiconductor device in or on a substrate with an externally accessible contact of the IC.

Each metal layer and each dielectric layer may consist of a number of stacked sub-layers, such as for instance in a CMOS 14 process in which stacks of Ti, TiN, AlCu, TiN may be used to define a single metal layer in the metallization stack. Similarly, the conductive conduits, e.g. vias, may be formed from more than a single material. For instance, in the aforementioned CMOS 14 technology, a via may be formed by a TiN liner and a W plug.

Each of the dielectric layers may also comprise more than a single layer. For instance, such a dielectric layer may be a stack comprising FSG (fluorosilicate glass), $SiO_2$ and HDP oxide (High Density Plasma) any other suitable dielectric material combination. Other suitable materials may also be used.

It is noted that the present invention is not limited to CMOS technologies only. Any technology in which a metallization stack is formed over a substrate is suitable for the integration of one or more embodiments of a thermal conductivity sensor as described in this application. Non-limiting examples of suitable alternative technologies include bipolar, BiCMOS, silicon-on-insulator, silicon-germanium based technologies and so on. Such alternative technologies may use metals and dielectric materials for the metallization stack that are different to the non-limiting examples for the CMOS 14 technology given above. For instance, other semiconductor processes may for instance use copper for the metal layers and vias.

Any suitable substrate may be used, such as a single crystal or polycrystalline silicon substrate, a silicon-germanium substrate, a silicon on insulator substrate and so on. The semiconductor devices in and/or on the substrate may take any suitable shape.

In the context of the present application, a thermal conductivity sensor is a sensor comprising at least one conductive filament, wire or other shape conductive element connected to circuitry in and/or on the substrate, which circuitry is arranged to provide the conductive element with a predefined current or voltage such as a predefined constant current or voltage, and which is adapted to determine the electrical resistance of the conductive element as a function of this predefined current or voltage.

In an embodiment, this may be achieved by a direct measurement of the resistance. In an alternative embodiment, this may be achieved by measuring the voltage across the conductive element as a function of a constant current and deriving the resistance from the measured voltage. In another alternative embodiment, this may be achieved by measuring the current across the conductive element as a function of a constant voltage and deriving the resistance from the measured current.

The thermal conductivity sensor may comprise a single conductive element or alternatively may comprise a plurality of conductive elements formed in the metallization stack comprising at least one heating element and at least one sensing element. In the case of one or more separate heating and sensing elements, the thermal conductivity sensor may be adapted to measure the heat transfer from the heating element to the sensing element through the fluid of interest. Each of the plurality of sensing elements may be conductively coupled to circuitry in or on the substrate to facilitate the determination of the resistance of the sensing element as previously explained. Alternatively, some of the sensing elements may be conductively coupled to external contacts of the IC to facilitate off-chip interrogation of the conductive element.

In an embodiment, the heating element is heated by an electrical current, and the electrical resistance of the one or more sensing elements is measured to determine to what extent the heating element has increased the temperature of the sensing element, as the resistance is temperature-dependent.

In an embodiment, at least some of the conductive elements of the plurality of conductive elements are formed in the same layer of the metallization stack, such that the spacing between the various conductive elements in the same layer can be varied as desired.

In a further embodiment, the conductive elements are formed in the upper metal layer of the metallization stack, as this requires the least amount of dielectric material to be removed from the metallization stack, thus avoiding potential issues with compromising the structural integrity of the metallization stack.

In an alternative embodiment, at least some of the conductive elements of the plurality of conductive elements are formed in different layers of the metallization stack, such that the minimal (vertical) distance between the conductive elements is governed by the individual thicknesses of the various layers of the metallization stack. The actual distance between the various conductive elements in different layers may be tuned by lateral displacement of these conductive elements with respect to each other.

At this point, it is noted that the sensitivity of the conductive elements can be increased by locating them in lower layers of the metallization stack, as the feature size of the elements in those layers is smaller than in the upper layers of the metallization stack. For optimized sensitivity (i.e. maximal resistance) long filaments or wires with small cross sections are required, which can be more readily achieved in the lower layers of the metallization stack, i.e. the layers closest to the substrate of the IC.

FIG. 1 schematically depicts a first embodiment of an IC comprising a thermal conductivity sensor. The IC comprises a substrate 10 on top of which a metallization stack 20 has been formed, which comprises dielectric layers 12 in between the metal layers 14. The dielectric layers 12 typically comprise conductive conduits (e.g. vias) for conductively connecting vertically displaced metal layer portions. Such conduit-comprising dielectric layers 12 will also be referred to as via layers. Further via layers, e.g. between the bottom metal layer 14 and the substrate 10, and/or between the upper metal layer 14 and the passivation stack 30 may also be provided. The passivation stack 30 may comprise a stack of passivation layers, which typically comprise dielectric materials such as silicon nitride and/or silicon oxide, although other materials may be equally feasible as will be apparent to the skilled person. In an alternative embodiment, the passivation stack 30 is replaced by a single passivation layer.

In the embodiment shown in FIG. 1, the upper metallization layer 14 has been patterned such that the thermal conductivity sensor comprises two conductive release structures in the form of a sensing element 16 and a heating element 18 laterally separated from each other by a distance d. The conductive release structures are suspended in a cavity 36 which may be formed by partial removal of the dielectric material of the passivation stack 20, e.g. through one or more etching steps as will be explained in more detail below.

The heating element 18 is typically conductively coupled to circuitry (not shown) for providing the heating element with a predefined current or voltage such as a known constant current or voltage, such that it is known how much heat per time unit is produced by the heating element 18 due to the fact that the dimensions and specific resistance of the heating element 18 are known. Optionally, the temperature of the heating element 18 may be determined as explained above.

The sensing element 16 is typically conductively coupled to circuitry (not shown) for providing the heating element with a predefined current or voltage such as a known constant current or voltage. The resistance of the sensing element 16 is determined as previously explained to establish the temperature of the sensing element 16. The difference in temperature of the heating element 18 and the sensing element 16 can be used to derive the thermal conductivity of the fluid medium in the cavity 36, such that the fluid medium can be identified, for instance by comparison of the calculated thermal conductivity with a library value in a library containing the respective thermal conductivities of a number of such fluid media. In an embodiment, such a library may be implemented on-chip in data storage circuitry such as a static random access memory, a look-up table, read-only memory and so on.

In an alternative embodiment, the composition of the gas mixture may be calculated using on-chip circuitry based on parameters that are determined using further sensors that may or may not be integrated on the same IC, e.g. temperature, relative humidity and pressure.

FIG. 2 depicts a number of non-limiting example embodiments of layouts of the conductive release structures. Layout (a) depicts the layout as shown in FIG. 1, in which both the sensing element 16 and the heating element 18 are wire-shaped and running parallel to each other in the same layer of the metallization stack 20 at a distance d.

In layout (b), a second sensing element 16' has been added to the design of the thermal conductivity sensor. The presence of multiple sensing elements 16, 16' at different distances d from the heating element 18 improves the resolution of the thermal conductivity sensor. One reason to include sensing elements 16, 16' with different spacings d to the heater 18 is that the pressure dependence of the thermal conductivity of gases increases for small dimensions. This is because at small dimensions the mean free path of the gas molecules (which depends on gas pressure) is important while at larger dimensions '>>mean free path' too many collisions occur, thus causing 'hot' gas molecules to equilibrate with other molecules before contacting the sensor element 16 or 16'. A similar effect is observed at relatively low gas pressures, where consequently the mean free path lengths increase considerably. By using sensing elements with different distances to the heating element 18 it is therefore possible to determine the gas pressure in addition to the gas composition, thus providing two sensing functionalities within a single sensing device.

The same principle can be used to monitor dynamic processes in the fluid, e.g. diffusion effects, as different time-dependent changes can be observed for the sensing elements at different distances.

The shape of the sensing element 16 and/or the heating element 18 is not limited to (straight) wire shapes. Any suitable shape may be contemplated. For instance, in order to increase the amount of heat transferred from the heating element 18 to the sensing element 16, an interdigitated layout as shown in layout (c), or an interdigitated meandering layout as shown in layout (d) may be chosen to increase the amount of thermal coupling between the heating element 18 and the sensing element 16. A meandering shape further increases the length and therefore the resistance of the heating element 18 and/or the sensing element 16, which means that based on the equation $R=R_0(1+a(T+T_0))$, it can be understood that larger signals can be measured upon a (fluid-induced) change in temperature of e.g. the sensing element 16.

Meandering sensing elements 16 and heating elements 18 may also be used in a non-interdigated fashion as shown in layout (e), in which the heating element 18 and the sensing element 16 are laterally separated by a distance d. In this embodiment, the total width $W_H$ of the heating element 18 and the total width $W_S$ of the sensing element 16 is preferably chosen such that $W_H \ll d$ and $W_S \ll d$ to prevent averaging effects between the heating element 18 and sensing element 16 dominating the effect of the distance d. In other words, as for instance the distance from the right hand side of the heating element 18 to the left hand side of the sensing element 16 is smaller than the distance from the left hand side of the heating element 18 to the right hand side of the sensing element 16, a large enough distance d between the sensing element 16 and the heating element 18 must be chosen to avoid these distance variations becoming dominant in the sensing result.

FIG. 3 shows an embodiment of a method to manufacture an IC comprising a thermal conductivity sensor. The left hand panes of FIG. 3 shows a cross section of the IC whereas the right hand panes of FIG. 3 show a 90° rotated cross section rotated along the dotted line in the left hand panes of FIG. 3. In step (a), an IC is provided comprising a substrate 10, a metallization stack 20 in which one of the metal layers (here the upper metal layer) is patterned to include a sensing element 16 and a heating element 18.

By way of non-limiting example, a connect structure 22 is also shown for providing a contact to the substrate 10, e.g. to a semiconductor device therein or thereon. Such a connect structure typically comprises a plurality of metal layers 26 separated by dielectric layers including conductive conduits such as vias 24 to conductively connect the various metal layers 26 with each other. The upper metal layer 26 may serve as a bond pad.

A passivation layer of stack of layers 30 is formed over the metallization stack 20 to protect the IC from external influences. The substrate, metallization stack and passivation layer may be formed in any suitable manner. As this may be achieved by many different techniques that are entirely routine to the skilled person, this will not be explained in further detail for the sake of brevity only.

In step (b), the passivation 30 is opened to create an opening 32 over the contact structure 22 and an opening 34 over the sensing element 16 and the heating element 18. Such openings may be created using any suitable etch recipe. As will be apparent to the skilled person, the openings 32 and 34 may be selectively formed using a (hard) mask (not shown) to protect those regions of the passivation 30 that are to remain on the IC. The opening of the passivation 30 to expose the contact structures 22, e.g. bond pads of the IC is entirely routine and has therefore not been explained further for the sake of brevity only.

In step (c), the sensing element 16 and the heating element 18 of the thermal conductivity sensor are released by the selective removal of the dielectric material surrounding these elements, thereby forming a cavity 36 in which the sensing element 16 and the heating element 18 are suspended. Any suitable selective etch recipe, such as a HF vapor etch or a liquid buffered HF etch may be applied. The passivation 30 and the upper metal portion 26 preferably are resistant to the applied etch recipe such that no additional measures to protect the passivation 30 and the upper metal portion 26 are required. Hence, a thermal conductivity sensor may be formed by adding only a single step (step (c)) to the routine manufacturing process of an IC.

The duration of the exposure of the IC to the etch recipe in step (c) is a factor in determining the dimensions of the cavity 36. Care has to be taken that the duration of the exposure does not compromise the structural integrity of the metallization stack 20 by the removal of excess dielectric material. The embodiment of the manufacturing method shown in FIG. 4 provides improved control over the dimensions of the cavity 36 at the expense of an additional processing step. Steps (a) and (b) are identical to steps (a) and (b) shown in FIG. 3 such that the aforementioned description of these steps equally applies.

In step (c), an additional conformal dry etch step is applied to remove the inter metal dielectric in between and underneath the sensing element 16 and the heating element 18 using the passivation 30 as hard mask or alternatively by forming a separate patterned resist mask (not shown) over the passivation 30, which may be removed following the dry etch step or the subsequent cavity 36 forming step (d) using a non-conformal etch recipe such as a vapor or liquid buffered HF etch. As the duration of the cavity forming etch step is reduced due to the fact that the cavity 36 is partially formed by dry etch step (c), better control over the dimensions of the cavity 36 is obtained, i.e. reducing the amount of under-etching, thereby improving the structural stability of the metallization stack 20 at the expense of an additional processing step.

In another embodiment of a method of manufacturing an IC with a thermal conductivity sensor as shown in FIG. 5, the metallization stack 20 comprises a metal plate 17 in a metal layer underneath the sensing element 16 and the heating element 18. Steps (a)-(c) are identical as explained with the aid of FIG. 3. In step (c), the metal plate 17 acts as an etch stop layer, thus preventing the uncontrolled etching in a vertical direction during the forming of cavity 36. This improves the stability of the metallization stack 20, although it cannot be avoided that the metal plate 17 will act as a heat sink, such that the sensitivity of the thermal conductivity sensor may be reduced by the presence of metal plate 17 due to the fact that less heat is transferred from the heating element 18 to the sensing element 16.

An alternative embodiment of a method of manufacturing an IC with a thermal conductivity sensor is shown in FIG. 6.

Here, the sensing element 16 and the heating element 18 are formed in one of the via layers 12, more particularly formed of the material used to form the conductive conduits 24, e.g. vias. In certain technologies, such as CMOS, tungsten may be used as the via metal, which has a higher specific resistance than most metals used in the metal layers 14 of the metallization stack 20, e.g. Al or Cu, such that a higher change in resistance can be measured upon a change in temperature of the sensing element 16, which translates to a larger signal, thus increasing the sensitivity of the sensing element 16.

As a practical point it is noted that although the formation of relatively large conductive structures in the via layers may violate the design rules of many foundries, several foundries will nevertheless allow such design rule violations such that the realization of the sensing element 16 and the heating element 18 are formed in one of the via layers 12 can be realized in most existing manufacturing facilities.

In FIG. 6, steps (a)-(c) are identical as explained with the aid of FIG. 3 with the only difference being that the sensing element 16 and the heating element 18 are formed in one of the via layers 12 such as the upper via layer 12.

In order to further improve the mechanical stability of the sensing element 16 or the heating element 18, such an element may be supported as in the embodiment shown in FIG. 7. In FIG. 7, steps (a)-(c) are identical as explained with the aid of FIG. 3 with the only difference being that at least one of the sensing element 16 and the heating element 18 is suspended in the cavity 36 whilst its ends are supported by the support pillars 28.

The support structures or pillars 28 ensure that the sensing element 16 or heating element 18 is held in place in case in of an excessive overetch in step (c) to the extent that the dielectric material 12 supporting the sensing element 16 or heating element 18 has been removed. The support pillars 28 may be formed using metal portions and inter-metal dielectric portions of the metallization stack 20, such that no additional process steps are required to form these support structures.

The added robustness of the sensing element 16 and/or heating element 18 of the thermal conductivity sensor comes at the cost of additional heat dissipation by the support pillars 28. As this causes a larger heat dissipation of the heat from the heating element 18 to the substrate, higher power consumption is required to maintain the sensitivity of the thermal conductivity sensor.

FIG. 8 schematically depicts a cross-section of an embodiment of an IC having a thermal conductivity sensor in accordance with layout (b) of FIG. 2, in which a first sensing element 16, a heating element 18 and a further sensing element 16' are suspended in the cavity 36, and wherein the distance between the first sensing element 16 and the heating element 18 is smaller than the distance between the further sensing element 16' and the heating element 18. In an embodiment, the first sensing element 16, heating element 18 and further sensing element 16' are formed in the upper metal layer of the metallization stack 20. In an alternative embodiment, the first sensing element 16, heating element 18 and further sensing element 16' are formed in the upper via layer of the metallization stack 20, although it is also feasible that the first sensing element 16, heating element 18 and further sensing element 16' are formed in a lower metal or via layer of the metallization stack 20.

As previously explained, although the sensing element(s) 16 and the heating element(s) 18 may all be formed in the same layer of the metallization stack 20, it is also feasible to form at least one of these elements in a different layer of the metallization stack 20. An embodiment of a method of manufacturing an IC comprising a thermal conductivity sensor having a sensing element 16 and a heating element 18 in different layers is shown in FIG. 9.

The left hand panes of FIG. 9 shows a cross section of the IC whereas the right hand panes of FIG. 9 show a 90° rotated cross section rotated along the dotted line in the left hand panes of FIG. 9. In FIG. 9, steps (a)-(c) are identical as explained with the aid of FIG. 3 with the only difference being that the heating element 18 is formed in a lower metal layer 14 than the sensing element 16. This may be achieved by the skilled person using routine metal layer patterning techniques such that this will not be explained in further detail for the sake of brevity only.

The IC obtained with the method of FIG. 9 may be particularly useful when the fluid to which the IC is exposed exhibits a substantial lateral flow, in which case the vertical separation of the sensing element 16 and the heating element 18 ensures that the thermal conductivity sensor is largely insensitive to such flow effects. Also, due to the fact that more than one layer of the passivation stack is used to form the various elements of the thermal conductivity sensor, a higher density of such elements can be obtained compared to a thermal conductivity sensor entirely formed in a single layer of the metallization stack 20.

It is not necessary to limit the formation of the various sensing and heating elements 16, 18 to different metal layers of the metallization stack 20 only. An alternative embodiment of a method to form an IC with a thermal conductivity sensor is shown in FIG. 10, in which a sensing element 16 is formed in a metal layer such as the upper metal layer of the metallization stack 20 and the heating element 18 is formed in a via layer such as the upper via layer of the metallization stack 20.

The left hand panes of FIG. 10 shows a cross section of the IC whereas the right hand panes of FIG. 10 show a 90° rotated cross section rotated along the dotted line in the left hand panes of FIG. 10. In FIG. 10, steps (a)-(c) are identical as explained with the aid of FIG. 3 with the only difference being that the heating element 18 is formed in a via layer instead of a metal layer. This may be achieved by the skilled person using routine metal layer patterning techniques such that this will not be explained in further detail for the sake of brevity only.

As will be apparent to the skilled person, although in FIGS. 9 and 10 the heating element 18 is located in between the sensing element 16 and the substrate 10, it is equally feasible to locate the sensing element 16 in between the heating element 18 and the substrate 10.

Other arrangements of the one or more sensing elements 16 and the one or more heating elements 18 will be immediately apparent to the skilled person. Some non-limiting examples of alternative embodiments of ICs having a thermal conductivity sensor in the metallization stack 20 are shown in FIG. 11-13.

In FIG. 11, two sensing elements 16 are located in a metal or via layer above a metal or via layer comprising the heating element 18. In an embodiment, each of the sensing elements 16 has a different distance to the heating element 18 such that this embodiment can be considered functionally equivalent to the layout (b) shown in FIG. 2 and the IC shown in FIG. 8.

In an alternative embodiment shown in FIG. 12, the heating element 18 is formed in a metal or via layer above the metal or via layer in which the pair of sensing elements 16 are formed, with each of the sensing elements 16 having the same distance to the heating element 18. Such an arrangement may for instance be suitable to compensate for lateral flow effects in the fluid to which the thermal conductivity sensor is exposed. Alternatively, the heating element 18 may be formed below the sensing elements 16.

In FIG. 13, multiple sensing elements 16 are placed equidistantly around a heating element 18 to improve the signal to noise ratio of the thermal conductivity sensor and/or to provide redundancy in case of the failure of one of the sensing elements 16.

Other layouts, e.g. comprising multiple heating elements 18 and/or multiple sensing elements 16 are equally feasible.

A non-limiting example of an operational mode of the thermal conductivity sensor according to at least some of the embodiments described herein is as follows. The thermal conductivity sensor is equilibrated in the absence of the fluid of interest, during which the heating element 18 is heated until thermal equilibrium is reached. During this equilibration process, the cavity 36 is typically filled with a known fluid composition.

Upon exposure of the thermal conductivity sensor to the fluid of interest, the known fluid in the cavity 36 is displaced by the fluid of interest, which different thermal conductivity properties will cause a shift towards new equilibrium, i.e. a change in the temperature and therefore the resistance of the sensing element 18, which change is measured and translated to a reading that is indicative of or proportional to the concentration and composition of the fluid of interest, such as a gas, e.g. Ar, $CH_2O$, $CO_2$, CO, He, Kr, $N_2$, $NO_2$, $N_2O$, NO, $O_2$, and so on.

In an alternative embodiment, at least some of the embodiments of the thermal conductivity sensor described in this application may also be used for thermal capacitance measurements to determine the composition of the gas mixture. This may be achieved by dynamic measurements in which voltage or current pulses are applied to the conductive element(s) whilst at the same time determining the time period it takes for the heating and/or sensing elements to equilibrate at the new temperature, which for instance may be derived from the time period in which the change in the resistance of the element under interrogation is completed. This period is a function of the thermal capacitance of the element(s) under interrogation as well as of the surrounding gas atmosphere (esp. when looking at heat transfer between 2 wires).

At this point it is noted that the cavity 36 as shown in the above described embodiments of the IC according to the present invention typically comprises an opening, e.g. through the passivation 30, through which it is in communicative contact with the environment of the IC. Although not explicitly shown in the above example embodiments, it should nevertheless be understood that the cavity 36 may comprise more than one opening, e.g. define a flow channel through at least a part of the IC, e.g. through at least a part of the metallization stack 20.

Also, although in the above example embodiments the heating element 18 and the sensing element 16 have been shown as discrete elements, it should nevertheless be understood that the heating element 16 and the sensing element 18 may be combined in a single element without departing from the teachings of the present application.

Moreover, it should be understood that at least some embodiments of the IC of the present invention may further comprise additional sensors, such as relative humidity sensors, temperature sensors, ambient light sensors and so on.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. An integrated circuit comprising:
   a substrate including semiconductor devices in or on the substrate; and
   a metallization stack over said semiconductor devices and over said substrate for interconnecting said semiconductor devices, the metallization stack comprising a cavity, and a thermal conductivity sensor comprising at least one conductive portion of said metallization stack suspended in said cavity;
   wherein the metallization stack comprises a multi-layered support structure for supporting at least the conductive portion.

2. The integrated circuit of claim 1, wherein at least some of the semiconducting devices define a control circuit for determining the resistance of the at least one conductive portion at a predefined voltage or current across the conductive portion.

3. The integrated circuit of claim 1, wherein the at least one conductive portion is formed in a metal layer or a via layer of the metallization stack.

4. The integrated circuit of claim 1, wherein the metallization stack comprises a metal plate located in between the at least one conductive portion and the substrate.

5. The integrated circuit of claim 1, wherein the thermal conductivity sensor comprises at least a pair of conductive portions including a sensing element and a heating element suspended in said cavity, said sensing element being thermally coupled to the heating element.

6. The integrated circuit of claim 5, wherein the sensing element and the heating element are formed in the same layer of the metallization stack.

7. The integrated circuit of claim 6, wherein the sensing element and the heating element are interdigitated.

8. The integrated circuit of claim 5, wherein the sensing element and the heating element are formed in different layers of the metallization stack.

9. The integrated circuit of claim 6, wherein at least one of the sensing element and the heating element is formed in a via layer.

10. The integrated circuit of claim 5, wherein the thermal conductivity sensor further comprises a further sensing element suspended in said cavity at a distance to the heating element that is different to the distance between the heating element and the sensing element.

11. The integrated circuit of claim 5, wherein the heating element has a meandering shape.

12. The integrated circuit of claim 1, wherein the conductive portion has a meandering shape.

13. An article comprising the integrated circuit of claim 1.

14. An integrated circuit comprising:
   a substrate including semiconductor devices in or on the substrate; and
   a metallization stack over said semiconductor devices and over said substrate for interconnecting said semiconductor devices, the metallization stack comprising multiple metal layers separated by a dielectric layer, the metallization layer including a thermal conductivity sensor formed therein, wherein at least one portion of the thermal conductivity sensor is formed in a metal layer of the metallization layer that is suspended in a cavity formed within the metallization layer;

wherein the metallization stack comprises a multi-layered support structure for supporting at least the conductive portion.

15. The integrated circuit device of claim 14 wherein the metal layer, in which the at least one portion of the thermal conductivity sensor is formed, is a tungsten layer.

* * * * *